United States Patent [19]

Modrovich

[11] 4,132,598

[45] Jan. 2, 1979

[54] STABILIZED LIQUID PHOSPHATE CONTAINING DIAGNOSTIC COMPOSITIONS AND METHOD OF PREPARING SAME

[76] Inventor: Ivan E. Modrovich, 1043 Mes Dr., Camarillo, Calif. 93010

[21] Appl. No.: 803,036

[22] Filed: Jun. 3, 1977

[51] Int. Cl.$^2$ .............................................. C12B 1/00
[52] U.S. Cl. ............................... 195/99; 195/103.5 R; 252/408
[58] Field of Search .................. 195/99, 103.5 R, 101; 252/408 R

[56] References Cited

U.S. PATENT DOCUMENTS

| | | | |
|---|---|---|---|
| 3,466,306 | 9/1969 | Babson | 195/103.5 R X |
| 3,540,984 | 11/1970 | Deutsch | 195/103.5 R |

*Primary Examiner*—Raymond N. Jones
*Assistant Examiner*—Robert J. Warden
*Attorney, Agent, or Firm*—Robert J. Schaap

[57] ABSTRACT

A stabilized liquid phosphate containing diagnostic composition and generally a phosphate containing substrate used in the determination of enzymes such as alkaline phosphatase and acid phosphatase. The composition actually includes a buffer composition containing a magnesium ion for activation of the enzyme and a substrate composition, which are mixed at time of determination. The buffer composition is of the proper pH so that when the buffer composition and the substrate composition are mixed, the resultant mixture will adopt the pH of the buffer composition. The stabilizer which is employed is one that will prevent hydrolysis of the phosphate from the organic substrate. Effective stabilizers include phenol and phenolic compounds and imidazole and nitro alaphatic compounds having from one through six carbon atoms.

47 Claims, No Drawings

STABILIZED LIQUID PHOSPHATE CONTAINING DIAGNOSTIC COMPOSITIONS AND METHOD OF PREPARING SAME

BACKGROUND OF THE INVENTION

I. Field of the Invention

This invention relates in general to certain new and useful improvements in the stabilization of diagnostic reagent compositions and the method of stabilizing, and, more particularly, to liquid stabilized phosphate-containing substrates in diagnostic reagent compositions and the method of stabilization.

II. Description of the Prior Art

It has recently been estimated that 25% of all in vitro diagnostic tests conducted annually in this country are not reliable. Unreliable tests can result in unnecessary medical treatment, the withholding of necessary treatment and lost income. Because of their high specificity, the use of enzyme determinations has significantly increased during the last few years and indications are that this trend will continue. However, rigorous quality control measures are required to assure the accuracy and consistency of results. This requirement stems from the fact that the exact nature of enzymes, as well as the mechanisms of their reaction, remains unknown for the most part.

At present, the greatest limitation in the diagnostic reagent manufacturer, by far, lies in the unstable characteristics of its product. Current methodologies require the use of numerous labile ingredients, and these ingredients are more likely to increase, rather than decrease, in number. Due to these severe restraints, rigorous quality control is required, and this quality control is, of course, costly. Moreover, if control in any step in the process is not maintained within high degree of control standards, the quality of the final product can be reduced materially.

Several diagnostic reagents containing organic groups and particularly diagnostic reagents containing organic aromatic or cyclic groups, along with hydrolizable phosphate groups, as for example, paranitrophenolphosphate, are used in the determination of various enzymes, such as those enzymes known as acid phosphatase and alkaline phosphatase. These enzymes, and particularly the alkaline phosphatase enzyme, are found in blood serum and are used for detecting abnormal conditions when present in an elevated state. The alkaline phosphatase enzyme is essentially a liver function enzyme, but is also found in bones and in bone portions of the body and in the intestines of human and animal bodies. Increased level of the alkaline phosphatase enzyme is generally indicative of liver malfunction. Acid phosphatase enzyme determination is also highly useful since it is derived from the prostate gland and is used for diagnosis of prostatic cancer.

The phosphatase enzymes are particularly effective for determination inasmuch as they have high affinity for phosphate groups which are attached to organic groups, and particularly to organic cyclic or aromatic groups, and will split the phosphate group from the remaining radical. Accordingly, measurement of alkaline phosphatase and acid phosphatase, for example, is made in the presence of a phospho-organic compound and also in the presence of magnesium ions. Measurement of the phosphate ions produced by reaction with the phosphate enzymes in a given time frame provides a fairly accurate determination.

Several approaches in the determination of the alkaline and acid phosphatase enzymes are commercially employed. In one reaction determination, alkaline phosphatase is determined by means of phenolphosphate in which the phenolphosphate, in presence of magnesium ions, is incubated along with the alkaline phosphatase. The resulting free phenol, due to the alkaline phosphatase activity, is measured after a time period in which the reaction has taken place. In like manner, glycerolphosphate may be used. One very common substrate which is used for determination with the phosphatase enzymes is paranitrophenolphosphate. In this case, a nitro group is attached to the phenol moiety in a para position and a phosphate group is attached to the phenol group by weak oxygen bonding. During the reaction with the alkaline phosphatase, the phosphate group is split, producing free paranitrophenol. The paranitrophenolphosphate is a colorless material at alkaline pH, whereas the nitrophenolphosphate is a yellow colored substance at alkaline pH.

These various substrates which are used in the determination of the alkaline phosphatase and the acid phosphatase are labile organic compounds in that they hydrolize in aqueous solutions and even in alcholic solutions and other organic solutions, thereby dissociating the phosphate group. Thus, substrates are considered labile from the standpoint that the phosphate is hydrolyzed in aqueous solution and hence the substrate does not retain its molecular properties. For this reason, in the present commercialization of alkaline phosphatase reagents and acid phosphatase reagents, a proper buffer is employed to establish the pH. Thus, the phosphate-containing compounds, such as the paranitrophenolphosphate, are provided in the dry state, even in the presence of the magnesium salt providing the magnesium ions. When making a determination, a buffer is added to the dry paranitrophenolphosphate, creating an aqueous solution of the buffer and the paranitrophenolphosphate with this resulting solution used to determine the activity of the phosphatase enzymes.

In accordance with the present invention, it has been found that it is possible to store the paranitrophenolphosphate and similar labile substrates in a liquid media in the presence of stabilizing reagents which effectively stabilize the paranitrophenolphosphate and similar labile components and keeps the phosphate group protected from hydrolysis in the liquid media.

The present commercial state of the art used for stabilizing the reactive ability of the substrates is by locking them into a solid matrix, either by freeze drying, or dry blending such as used for tableting dried powders, primarily in the pharmaceutical diagnostic and related industries and immobilization by locking the chemical structure of the substrate in a solid matrix. Contrary to the sophistication these terms imply, these approaches are neither practical nor desirable and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending, and usefulness of the product is further limited by packaging modes and sizes.

Furthermore, good product uniformity is difficult to achieve. This condition is exemplified by the fact that most commercial freeze dried control sera (reference serum) list the acceptable bottle-to-bottle variation of enzyme constituents at ± 10% of the mean.

The present invention is uniquely designed so that the labile ingredients in a liquid reagent solution are effectively "stabilized" by inhibiting hydrolization of the phosphate group forming part of the substrate, thereby controlling the activity of the labile ingredients in a liquid solution against reactivity. This means of stabilization ensures long-term stability in a liquid media. Moreover, close tolerance control can be achieved in the manufacturing of a high quality product which eliminates the inconvenience of the rigid package size and the high cost of packaging and freeze drying and reagent waste.

OBJECTS OF THE INVENTION

It is, therefore, the primary object of the present invention to provide a liquid organic diagnostic reagent composition containing a labile compound having a phosphate group and cyclic or aromatic group and which is stabilized in a container against hydrolysis.

It is an additional object of the present invention to provide a stabilized composition of the type stated in a container which has execellent shelf life and which container may be repeatedly opened without substantial degradation of the labile components therein.

It is another object of the present invention to provide a labile composition of the type stated containing components which may be stored in a liquid media, and are used in the determination of alkaline phosphatase and acid phosphatase and related enzymes and which compositions are stabilized against degradation.

It is a further object of the present invention to provide a liquid stabilized composition of the type stated in which the labile components are present in an aqueous or organic solvent media and where the stabilization of the labile components does not affect reactivity after a substantial period of time.

It is also an object of the present invention to provide a method of stabilizing organic diagnostic reagent compositions containing a labile compound having a hydrolizable phosphate group in a liquid media with relatively low-cost, commercially available stabilizing ingredients.

It is another salient object of the present invention to provide a method of stabilizing compositions of the type stated and which composition have a long shelf life and reactivity of the labile components are not substantially affected.

It is yet another object of the present invention to provide a method of stabilizing compositions of the type stated with labile components in the presence of a liquid media for a substantial period of time at a relatively low cost and with a high degree of composition purity.

With the above and other objects in view, my invention resides in the novel compositions and the methods of making the same as hereinafter described in more detail.

SUMMARY OF THE INVENTION

Labile organic substrates containing a phosphate radical and particularly such substrate having an aromatic or cyclic group and a phosphate radical are treated according to the invention, resulting in long-term stability without affecting reactivity or photometric absorptivity. The invention provides reagents where quality control is assured throughout manufacturing, packaging, storage and use. The inconvenience of rigid package size is eliminated as is the high cost of packaging, freeze-drying and reagent waste. Liquid diagnostic reagent compositions of this type provide enzyme determination with application flexibility.

The stabilized liquid diagnostic compositions of the invention when assessed in studies compare with respective liquid reagent compositions freshly prepared. These studies can show a 1:1 correlation between aged liquid and fresh reagents with comparable sensitivity and precision. Providing reagents of this type in a stable liquid form enhances the colorimetric applicability of present day methodologies, as well as other non-colorimetric methodologies. Stable liquid reagents are especially advantageous where substrate consumption and reactivity rates are the basis of measurement. The liquid system of the present invention also offers better reagent homogeneity and packaging, as well as flexibility in usage, in contrast to the freeze dried or dry media preparations.

In diagnostic reagent determination, the stabilization of the labile components and particularly a highly reactive and degradative substrate in a ready-to-use liquid media is a new and exciting approach to satisfy the needs of the clinical laboratory and the reliability demands of the regulatory authorities. The flexibility of these liquid reagent systems ensures their applicability to automated instrumentation, as well as their convenience in manual testings.

Enzymes are large molecular weight, complex protein molecules, usually of unknown chemical structure. They are presently classified by their catalytic activity and extreme substrate specificity. Enzymes may be redefined as biological catalysts, capable of catlyzing a reaction of a single substrate, or a reaction of a similar group of substrates.

In some cases, coenzymes may be present in the determination reaction. Coenzymes are lower molecular weight organic chemicals of well-defined structure, whose reactions or interactions may be necessary or desirable for specific enzyme assay or reaction. They are catalyzed resulting in an irreversible change in the coenzyme's structure and/or atomic composition. Coenzymes are very useful in clinical assay procedure. Some have strong absorbance, their reactions are stiochiometric with the substrate and, therefore, the creation or disappearance of the absorbing form can be followed photometrically.

Substrates are organic chemicals of known structure, whose reactions or interactions are catalyzed by enzymes resulting in a change in the compound's structure, atomic composition, or stereo-chemical rotation. In general, substrates are prone to microbiological degradation as they serve as food for bacteria, fungi, and other microorganisms. In the case of the present invention, these substrate compounds are unstable in aqueous media or other liquid media. Typical substrates which may be used in the present invention are, for example, glycerol phosphate, phenol phosphate and paranitrophenolphosphate, thymolphthaline phosphate, and usually the monosodium phosphate thereof, and the like.

The reagents of the present invention are used for determining those enzymes, such as acid phosphatase and alkaline phosphatase, which react with a substrate stabilized in accordance with this invention. As indicated previously, those substrates which are stabilized in the liquid media contain a phosphate group hydrolizable from an organic group and preferably an aromatic or cyclic group. Thus, in the case of paranitrophenolphosphate, which is a simple organic molecule, the nitro group is attached to the phenol group in the para position and a phosphate group is attached to the phenol group by weak oxygen bonding. During the course of the reaction with the enzyme, the phosphate group will split from the molecule, producing a free phosphate and a free paranitrophenol. The alkaline phosphatase enzyme will split the phosphate group from the substrate at an alkaline pH and, in like manner, the acid phosphatase will split the phosphate group from the substrate in an acid pH.

Substrates of this type, as for example, the paranitrophenolphosphate, are very labile organic compounds in that the phosphate group will hydrolize in an aqueous or even alcoholic solution, thus rendering the substrate ineffective for enzyme determination. For this reason, in the present commercialization of alkaline phosphatase reagents, an alkaline buffer, usually an AMP buffer (2-amine-2-methyl-1-propanol) and the paranitrophenolphosphate are mixed. The buffer is normally liquid and, on use, the PNPP, which is a dry material, is then mixed into solution, usually in an aqueous media, and the solution is used to test enzyme activity. In accordance with the present invention, a buffer is added in an amount to adjust the pH to a proper pH level. Thus, for example, in the case of stabilizing the substrate for use in alkaline phosphatase determination, the substrate is protected from hydrolysis by a stabilizing compound, such as phenol, which protects the phosphate group from hydrolysis even at elevated temperatures.

After the liquid stabilized solution is prepared, it is then dispensed into amber glass bottles and which are sealed in an air-tight condition. Moreover, these bottles are typically stored under refrigeration. The projected shelf life of the stabilized enzymes and coenzymes is up to one to two years under these conditions without appreciable degradation.

It has been found in accordance with the present invention that the dissolved components exhibit good solubility and stability in the aqueous media. The understood chemical or physical reaction which provides for the stabilization of the labile components is more fully described hereinafter.

These and other features and attendant advantages of the invention will become apparent as the invention becomes better understood by reference to the following general description and the following detailed description.

DETAILED DESCRIPTION

In the clinical diagnostic field, the commercial application of the present invention is represented by, but not limited to, the diagnostic reagents used to determine enzyme concentration, as for example, alkaline phosphatase concentrations in biological fluids, and the like. Nevertheless, compositions prepared in accordance with the present invention can be used to determine and quantitate other biological constituents, as for example, acid phosphatase (ACP) or alkaline phosphokinase (ALP), and the like, in biological fluids.

These above-identified enzymes often react similarly with respect to the substrates of the present invention and some of the chemical reactions involved are common. The above enzymes are only exemplary and it should be understood that other enzymes may be determined in accordance with the present invention. The following chemical reaction scheme is presented as a model to illustrate the general nature of the reactions involved:

REACTION SCHEME 1 — GENERAL MODEL

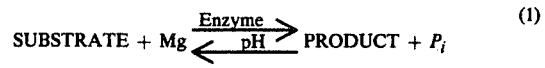

REACTION SCHEME 2 — SPECIFIC MODEL

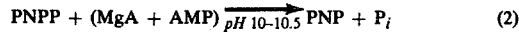

REACTION SCHEME 3 — SPECIFIC MODEL

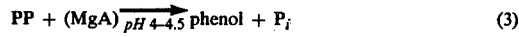

Symbols have been used in the above reaction schemes for purposes of clarity and those symbols are identified as follows:
PNPP: paranitrophenolphosphate
MgA: magnesium aspertate
AMP: 2-amino-2-methyl-1-propanol
PNP: paranitrophenol
$P_i$: a phosphate group, usually $PO_4$
PP: phenolphosphate In the above reaction schemes, the general model shows that the substrate is usually combined with a buffer in the reaction determination for a particular enzyme and produces a product as well as a phosphate group. As indicated, the phosphate group would normally be $PO_4$ which depends upon the amount of the buffer used and the particular reaction components. The phosphate group may be present as an ion in solution, or otherwise attached to the buffer which, in this latter case, would act as a receptor for the phosphate group.

Reaction Scheme 2 illustrates a specific model for alkaline phosphatase determination. In this case, it can be observed that a magnesium salt, such as magnesium aspertate, is present to activate the enzyme. The third reaction scheme discloses a specific model for acid phosphatase determination.

In accordance with the present invention, the substrate composition is separated from the buffer composition and is included in a different container the composition being mixed at the time of determination. Thus, the substrate and a stabilizer in a liquid media are contained in one container and the buffer and the magnesium compound in a liquid media are introduced into another container.

The buffering composition will contain a suitable buffering agent, as for example, AMP. The AMP buffer is preferably used in connection with the determination of the alkaline phosphatase enzyme. However, other buffering agents may be used, preferably amino organic buffering agents, including diethylamine, and triethylamine, a tris buffer for example. Non-organic buffering agents may also be employed and include, for example, sodium carbonate and sodium bicarbonate. It is important for the buffering agent to provide the desired pH range in the stabilized composition. In some cases, it may be desirable to add an acid such as hydrochloric acid, acetic acid, succinic acid, etc. to adjust the pH to the desired level.

The buffering agent for the acid phosphatase reagent composition may include various salts and acids which would provide an acid pH in the stabilized composition. Thus, for example, sodium acetate, acetic, acid, sodium chloride-hydrochloric acid buffer solutions and "PIPES" buffer may be used.

The magnesium salt is designed to activate the enzyme when in solution, and will also be included in the buffer composition. The magnesium salt included in the buffer composition is preferably magnesium aspertate since there does not appear to be any precipitation of magnesium. However, other magnesium salts may be used and include, for example, magnesium chloride, magnesium acetate, magnesium fluoride and possible magnesium citrate. Other buffers which may be used in the present invention, at least for the alkaline phosphatase enzyme determinations, include diethanolamine and sodium carbonate.

The buffer which provides the proper pH ranges should not materially interfere with the phosphatase activity. In the case of the reagent composition for determination of alkaline phosphatase, the buffer should preferably provide a pH of about 10.0 to 10.5, although the pH can range from about 9.5 to 10.7. In fact, the pH range can extend from about 9 to about 12, although at pH levels below 10.0 and above 10.7, the buffering capacity will decrease. In the case of the reagent compositions for the acid phosphatase, the pH should preferably be in the range of about 4.0 to 4.5, although the pH could preferably be in the range from about 3.5 to 4.8. However, while pH can be less than 3.6 and somewhat slightly greater than 4.8, again the buffering capacity will decrease.

The magnesium compound is present in the buffer composition in about a 10 millimolar concentration, although the concentration can range from about 0.5 millimoler to about 50 millimoler if required. The buffer, and particularly the AMP buffer, is present in about 0.8 moles, although the buffer may range from about 0.05 moles to about 2 moles.

The substrate is present in the substrate composition along with a stabilizing agent of the type hereinafter described in more detail. One of the preferred stabilizing agents is phenol, although other stabilizing agents, as hereinafter described, could also be employed. In this substrate composition, the substrate, as for example, the PNPP, will exist in about 100 millimoles in solution up to a saturation point of about 1 mole. Preferably, the PNPP should be present in the range of about 2 millimoles to about 0.8 moles in the substrate composition. The phenol will be present in about the same range, although phenol can be present in at least twice the amount of the substrate in the substrate composition. Water will then generally make up the remainder of the stabilized substrate composition.

A suitable buffering agent may also be included in the substrate composition, as for example, triethanolamine, trihydroxyamine, etc. to adjust the pH of the substrate composition to about 8.0 to about 9.5 and preferably about 8.5 to about 9.0. The substrate composition is added to the buffer composition at time of determination, in relatively small amounts so that the pH of the final mixture of the two compositions will adopt that of the buffer composition. The buffering agent such as the triethanolamine will also serve as a solubilizing agent for the phenol or other stabilizer in the substrate composition, which is effective to solubilize the phenol at higher concentrations. In the absence of this buffering agent at higher concentrations, the phenol may tend to form an aqueous layer and a phenol layer, as a two-phase solution.

A number of other substrates which may be stabilized in accordance with the present invention and include, for example, salts of PNPP, e.g. the sodium salt or the dicyclohexylamine salt. In addition, di-[(tris-hydroxymethol)aminomethane] salt; P-nitrophenolphosphate dicyclohexylammonium salt; P-nitrophenolphosphate di[2-amino-2-ethyl-1,3-propanediol] salt; and P-nitrophenolphosphate, disodium salt, hexahydrate may also be used.

In addition to phenol, the stabilizer may also include various phenolic compounds which are also effective as stabilizers, as for example, phenolic compounds including the sulfate group, e.g. parasulfophenyl and parasulfonic acid phenyl, etc. It has also been recognized in accordance with the present invention that stabilizing agents other than phenol can be used and include for example, imidazol, which is often referred to as "glyoxalin", namely $C_3H_4N_2$. It has been recognized that various nitro-aliphatic compounds having from one through six carbon atoms, such as nitromethane, nitroethane, etc., are also somewhat effective as stabilizers, although the nitro-aliphatic compounds are less effective than phenol and phenolic compounds. Phosphate compounds generally are not necessarily effective stabilizers inasmuch as they precipate along with a magnesium salt.

When the buffer is dissolved in water, a suitable bacteriostate, such as an azide compound, e.g. sodium azide, may be added, preferably in amount of about 0.1% w/w/ However, the amount of azide compound or other bacteriostat which is added can range from 0.01% to about 0.5%. It has been found in accordance with the present invention that the azide compound exhibits the result of aiding in the stability of the composition. In addition, other bacterical or other fungicidal agents which do not chemically react with the buffer or inhibit the enzymatic reaction may be employed. For example, some of these agents which may be used in addition to sodium azide are benzoic acid, thymol or pentachlorophenol. In many cases, especially with high pH buffers, the bacteriostat is not necessary and can be eliminated.

The actual mechanism of stabilization is not fully understood. Although it is recognized that the hydrolization of the phosphate in the aqueous media will occur until an equilibrium is achieved. It is understood that the hydrolysis reaction is affected by the reaction constant of hydrolysis K. Thus, the hydrolysis reaction can be represented by:

$$(R - PO_4) + H^+ \rightarrow R^+ + PO_4$$

where R—PO$_4$ represents the organic compound having a phosphate group and R$^+$ represents the compound with the phosphate group hydrolized therefrom:

The reaction constant K is represented by and determined in accordance with:

$$K = \frac{[R^+][PO_4^-]}{[R - PO_4][H^+]}$$

In accordance with the above, the reaction can be retarded by overloading the reaction products with R$^+$ or PO$_4^-$ or both. To overload the reaction media with PO$_4^-$ may affect the reaction of the enzymes in a determination reaction. The hydrolysis reaction appears to take place to an equilibrium saturation unless otherwise stabilized and it is further recognized that the stabilizer provides the same effect as the reaction products so that the phenol and the other stabilizers effectively inhibit hydrolization of compounds such as the PNPP.

Thus, the stabilizer which is used in the present invention is one which would provide the same effect in the reaction media as the $PO_4^-$ or the $R^+$. In this way, the stabilizer acts as an excess of $PO_4^-$ or $R^+$ and thereby inhibits the hydrolization reaction. Thus, in terms of hydrolization, the stabilizer should be sufficiently close to the actual $R^+$ for example, at least in effect in solution. However, in the actual enzyme determination, the enzyme is very specific and will only be affected by the substrate and the specific end product and will not be affected by the stabilizer.

It has been found that the substrate, when stabilized in accordance with the present invention, has a surprising stability of up to 18 months to two years at about 4° C. or under refrigeration temperatures. Even moreso, the substrate composition is almost fully stabilized for up to two to three months at room temperatures. At higher temperatures, the degradation, that is the hydrolysis of the phosphate group on the substrate, takes place at an accelerated rate. Once the substrate composition is mixed with the buffered composition, the stability of the resulting mixture is limited due to the fact that in the mixed solutions that phosphate group will hydrolize much more readily. When in the mixed form, the stability is about two weeks under refrigeration temperatures and usually about no more than two days at room temperatures.

In use, the substrate composition is added to the buffer composition either by a known quantity amount or dropwise, whichever is preferable. The resulting solution is then mixed and used at room temperature for the determination of phosphatase enzyme activity by adding the phosphatase enzyme to the mixed compositions. The final solution of the two compositions prior to analysis contains the alkaline buffer within the desired pH range as specified above, the magnesium salt and the substrate, along with the stabilizing agent.

In the final composition, the magnesium salt will be present in the range of about 0.5 millimolers up to about 50 millimolers, and the substrate will be present at a concentration of no less than 0.5 millimolers up to about a concentration of about 30 millimolers. It has been found that the phenol or other stabilizing agent, along with the solubilizing agents, such as the triethanolamine, which effectively operates as a solubilizing agent does not interfere with phosphatase enzyme determination. It has also been found that the phenol at very high concentrations does inhibit the reaction somewhat, but only to a negligible extent. The solubilizing agent is included in the liquid substrate composition to prevent phase separation of the stabilizing agent.

When the substrate composition and the buffer composition have been mixed, the body fluid sample which contains the phosphatase enzyme is thereupon added to the resulting mixed solution. The alkaline phosphatase activity is determined at about 405 nanometers at constant temperature. The constant temperature may range anywhere from about room temperature, 25° C., or even lower, such as 20° C., up to 40° C. or even 50° C. Above 50° C., the alkaline phosphatase enzymes appear to denature, thereby rendering the determination impractical.

The substrate solution as prepared in its stabilized form is sensitive to light and is therefore normally packaged in dark or amber bottles, and these bottles may be formed of any material which does not react with the substrate composition, as for example, plastic or glass.

The invention is further illustrated by, but not limited to, the following Examples.

EXAMPLES

EXAMPLE 1

0.8 moles of an AMP buffer is added to magnesium aspertate in an aqueous medium and is adjusted to a pH of about 10.2 with a slight amount of hydrochloric acid to form a buffer composition.

Paranitrophenolphosphate is then combined with phenol in the dry form and added to an aqueous solution such that the paranitrophenolphosphate is present in about 1 mole and the phenol is present in the amount of about 1.5 moles. Triethanolamine is also added to adjust the pH of about 8.6 and to further retard the hydrolysis of the paranitrophenolphosphate. The remaining solution is made up of distilled water to form a substrate composition.

After complete solution is attained, the buffer solution is added to a plastic or glass container which is then closed. In like manner, the substrate solution is then added to a plastic or glass amber container which is then closed. The containers are then sealed and stored under refrigeration. It has been found that a stabilized composition in this manner provides storage stability of up to two years without significant degradation.

EXAMPLE 2

The substrate composition and the buffer composition produced in accordance with Example 1 are then mixed and a body fluid containing alkaline phosphatase is added to this composition. The phenol stabilizer does not appear to affect the reaction with respect to the alkaline phosphatase. The phosphate group of the paranitrophenol is split from the paranitrophenolphosphate and provides a basis of determination of the alkaline phosphatase.

EXAMPLE 3

Magnesium acetate is substituted for the magnesium aspertate in Example 1 and again is present in substantially the same amount as the magnesium aspertate. Again, the composition exhibited the same long shelf-life without any substantial degradation.

EXAMPLE 4

Magnesium chloride is substituted for the magnesium aspertate in Example 1 and again is present in substantially the same amount as the magnesium aspertate. Again, the composition exhibited the same long shelf-life without any substantial degradation.

EXAMPLE 5

Triethynolamine is substituted for the AMP of Example 1 and is also present in substantially the same amount as the AMP in Example 1. In this case, the substrate composition exhibited the same long shelf-life without any substantial degradation.

EXAMPLE 6

Parasulfophenyl is substituted for the phenol in Example 1 and again is present in substantially the same amount as the phenol. Again, the composition exhibited the same long shelf-life without any substantial degradation.

EXAMPLE 7

Imidazol is substituted for the phenol of Example 1 and is also present in substantially the same amount as the phenol in Example 1. In this case, the substrate composition exhibited the same long shelf-life without any substantial degradation.

It is to be realized that only preferred embodiments of the invention have been described and that numerous substitutions, modifications and alterations are permissible without departing from the spirit and scope of the invention as defined in the following claims.

Having thus described my invention, what I desire to claim and secure by letters patent is:

1. A method of stabilizing a labile organic diagnostic reagent compound against hydrolysis in an aqueous solution and which compound contains a cyclic or aromatic group with a phosphate moiety thereon, said method comprising mixing said reagent compound with a stabilizing agent selected from the class consisting of (1) phenol and phenolic compounds, (2) imidazol and (3) nitro aliphatic groups containing from 1 to 6 carbon atoms, said stabilizing agent approximating the effect of the cyclic or aromatic group without the phosphate moiety thereon as a reaction product or portion thereof in a hydrolysis reaction, or the effect of the phosphate moiety which would be produced in a hydrolysis reaction, and which thereby inhibits a hydrolization reaction of said compound, introducing the mixed reagent compound and stabilizing agent into a water containing liquid to form an aqueous solution thereof, and storing said solution.

2. The method of claim 1 further characterized in that said method comprises mixing a buffer compound with a magnesium compound to form a mixture thereof, and introducing said mixture into a water containing liquid to form an aqueous buffer composition such that the buffer compound is present in the buffer composition to create a proper pH within the desired range for a phosphatase enzyme determination.

3. The method of claim 2 further characterized in that said magnesium compound is magnesium aspertate.

4. The method of claim 1 further characterized in that said method comprises mixing a buffer compound with a magnesium compound to form a mixture thereof, and introducing said mixture into a water containing liquid to form an aqueous buffer composition such that the buffer compound is present in the buffer composition to create an alkaline pH within the range of 9.5 to 10.7 for determination of alkaline phosphatase.

5. The method of claim 1 further characterized in that said method comprises mixing a buffer compound with a magnesium compound to form a mixture thereof, and introducing said mixture into a water containing liquid to form an aqueous buffer composition such that the buffer compound is present in the buffer composition to create an alkaline pH within the range of 10.0 to 10.5 for determination of alkaline phosphatase.

6. The method of claim 1 further characterized in that said method comprises mixing a buffer compound with a magnesium compound to form a mixture thereof, and introducing said mixture into a water containing liquid to form an aqueous buffer composition such that the buffer compound is present in the buffer composition to create an acid pH within the range of 3.5 to 4.8 for determination of acid phosphatase.

7. The method of claim 1 further characterized in that said method comprises mixing a buffer compound with a magnesium compound to form a mixture thereof, and introducing said mixture into a water containing liquid to form an aqueous buffer composition such that the buffer compound is present in the buffer composition to create an acid pH within the range of 4.0 to 4.5 for determination of acid phosphatase.

8. The method of claim 1 further characterized in that said stabilizing agent is phenol and phenolic compounds.

9. The method of claim 1 further characterized in that said diagnostic reagent compound is a labile substrate used in determination of a phosphatase enzyme.

10. The method of claim 8 further characterized in that a solubilizing agent is included in the liquid solution to prevent phase separation of the stabilizing agent.

11. The method of claim 8 further characterized in that said substrate is paranitrophenolphosphate.

12. The method of claim 1 further characterized in that said diagnostic reagent compound is a labile substrate used in phosphatase enzyme determination, said substrate is paranithrophenolphosphate, and said stabilizing agent is phenol and phenolic compounds.

13. A composition comprising a labile organic diagnostic reagent compound stabilized against hydrolysis in an aqueous solution, said compound containing a cyclic or aromatic group with a phosphate moiety thereon, said compound being stabilized in the presence of a stabilizing agent selected from the class consisting of (1) phenol and phenolic compounds, (2) imidazol and (3) nitro aliphatic groups containing from 1 to 6 carbon atoms, said stabilizing agent approximating the effect of the cyclic or aromatic group without the phosphate moiety thereon as a reaction product or portion thereof in a hydrolysis reaction, or the effect of the phosphate moiety which would be produced in a hydrolysis reaction, and which thereby inhibits a hydrolization reaction of said compound, and a water containing liquid in which the mixed reagent compound and stabilizing agent are substantially disolved to form the aqueous composition thereof.

14. The composition of claim 13 further characterized in that said composition is used in conjunction with a buffer composition comprised of a mixture of a buffer compound and a magnesium compound, said mixture being present in a water containing liquid to form an aqueous buffer composition such that the buffer compound is present in the buffer composition to create a proper pH range for a phosphatase enzyme determination.

15. The buffer composition of claim 14 further characterized in that the pH range is 9.5 to 10.7 for alkaline phosphatase determination.

16. The buffer composition of claim 14 further characterized in that the pH range is 10.0 to 10.5 for alkaline phosphatase determination.

17. The buffer composition of claim 14 further characterized in that the pH range is 3.5 to 4.8 for acid phosphatase determination.

18. The buffer composition of claim 14 further characterized in that the pH range is 4.0 to 4.5 for acid phosphatase determination.

19. The composition of claim 14 further characterized in that said substrate is paranitrophenolphosphate.

20. The buffer composition of claim 14 further characterized in that said magnesium compound is magnesium aspertate.

21. The composition of claim 13 further characterized in that said stabilizing agent is phenol and phenolic compounds.

22. A method of preparing aqueous liquid reagent systems used in phosphatase enzyme determination, said method comprising forming a substrate composition by stabilizing a labile organic diagnostic reagent substrate against hydrolysis and which substrate contains a cyclic or aromatic group with a phosphate moiety thereon, said method comprising mixing said reagent substrate with a stabilizing agent selected from the class consisting of (1) phenol and phenolic compounds, (2) imidazol and (3) nitro aliphatic groups containing from 1 to 6 carbon atoms, said stabilizing agent approximating the effect of the cyclic or aromatic group without the phosphate moiety thereon as a reaction product or portion thereof in a hydrolysis reaction, or the effect of the phosphate moiety which would be produced in a hydrolysis reaction, and which thereby inhibits a hydrolization reaction of said substrate, said substrate being specific with respect to a phosphatase enzyme such that the enzyme will be affected by the substrate or the end product in a determination reaction or both and will not be affected by the stabilizing agent, introducing the mixed reagent substrate and stabilizing agent into a water containing liquid to form an aqueous solution thereof, storing said solution in a container, said method further comprising preparing a buffer composition by mixing a buffer compound with a magnesium compound, and introducing said mixture of buffer compound and magnesium compound into a water containing liquid to form an aqueous buffer composition and in which the buffer compound is present in an amount to create a proper pH range for a phosphatase enzyme determination, and storing said buffer composition in another container.

23. The method of claim 22 further characterized in that said stabilizing agent is phenol and phenolic compounds.

24. The method of claim 23 further characterized in that a solubilizing agent is included in the aqueous solution of substrate and stabilizing agent to prevent phase separation of the stabilizing agent.

25. The method of claim 22 further characterized in that said substrate is paranithrophenolphosphate and said stabilizing agent is phenol and phenolic compounds.

26. A stabilized liquid reagent used in phosphatase enzyme determination, said system comprising a substrate composition comprised of a labile organic diagnostic reagent substrate stabilized against hydrolysis in an aqueous solution, said substrate containing a cyclic or aromatic group with a phosphate moiety thereon, said reagent substrate being stabilized in the presence of a stabilizing agent selected from the class consisting of (1) phenol and phenolic compounds, (2) imidazol and (3) nitro aliphatic groups containing from 1 to 6 carbon atoms, said stabilizing agent approximating the effect of the cyclic or aromatic group without the phosphate moiety thereon as a reaction product or portion thereof in a hydrolysis reaction, or the effect of the phosphate moiety which would be produced in a hydrolysis reaction, and which thereby inhibits a hydrolization reaction of said substrate, said substrate being specific with respect to a phosphatase enzyme such that the enzyme will be affected by the substrate or the end product in a determination reaction or both and will not be affected by the stabilizing agent, the mixed reagent substrate and stabilizing agent being substantially dissolved in a water containing liquid to form an aqueous solution thereof, said solution being stored in a container, and said reagent system comprising an aqueous buffer composition comprised of a mixture of a buffer compound and a magnesium compound in a water containing liquid to form said aqueous buffer composition, said buffer compound being present in an amount to create a proper pH range for a phosphatase enzyme determination, said buffer composition being stored in another container.

27. The method of claim 26 further characterized in that said stabilizing agent is phenol and phenolic compounds.

28. The composition of claim 26 further characterized in that said diagnostic reagent compound is a labile substrate used in determination of a phosphatase enzyme, said substrate is paranithrophenolphosphate and said stabilizing agent is phenol and phenolic compounds.

29. A method of stabilizing a labile organic diagnostic reagent compound against hydrolysis in an aqueous solution and which compound contains a cyclic group or aromatic group with a nitro group and a phosphate group attached thereto by weak oxygen bonding, said method comprising mixing said reagent compound with a stabilizing agent selected from the class consisting of (1) phenol and phenolic compounds, (2) imidazol and (3) nitro aliphatic groups containing from 1 to 6 carbon atom, said stabilizing agent approximating the effect of the cyclic or aromatic group without the phosphate moiety thereon as a reaction product or portion thereof in a hydrolysis reaction, or the effect of the phosphate moiety which would be produced in a hydrolysis reaction, and which thereby inhibits a hydrolization reaction of said compound, introducing the mixed reagent compound and stabilizing agent into a water containing liquid to form an aqueous solution, and storing said solution.

30. The method of claim 29 further characterized in that said method comprises mixing a buffer compound with a magnesium compound to form a mixture thereof and introducing said mixture into a water containing liquid to form an aqueous buffer composition such that the buffer compound is present in the buffer composition to create a proper pH within the desired range for a phosphatase enzyme determination.

31. The method of claim 29 further characterized in that said method comprises mixing a buffer compound with a magnesium compound to form a mixture thereof and introducing said mixture into a water containing liquid to form an aqueous buffer composition such that the buffer compound is present in the buffer composition to create an alkaline pH within the range of 9.5 to 10.7 for determination of alkaline phosphatase.

32. The method of claim 29 further characterized in that said method comprises mixing a buffer compound with a magnesium compound to form a mixture thereof and introducing said mixture into a water containing liquid to form an aqueous buffer composition such that the buffer compound is present in the buffer composition to create an acid pH within the range of 3.5 to 4.8 for determination of acid phosphatase.

33. The method of claim 29 further characterized in that said stabilizing agent is phenol and phenolic compounds.

34. The method of claim 29 further characterized in that said diagnostic reagent compound is a labile substrate used in determination of a phosphatase enzyme, said labile substrate is paranithrophenolphosphate and said stabilizing agent is phenol and phenolic compounds.

35. A composition comprising a labile organic diagnostic reagent compound stabilized against hydrolysis in an aqueous solution, said compound containing a cyclic group or aromatic group with a nitro group and phosphate group attached thereto by weak oxygen bonding, said compound being stabilized in the presence of a stabilizing agent selected from the class consisting of (1) phenol and phenolic compounds, (2) imidazol and (3) nitro aliphatic groups containing from 1 to 6 carbon atoms, said stabilizing agent approximating the effect of the cyclic or aromatic group without the phosphate moiety thereon as a reaction product or portion thereof in a hydrolysis reaction, or the effect of the phosphate moiety which would be produced in a hydrolysis reaction, and which thereby inhibits a hydrolization reaction of said substrate, and a water containing liquid in which the mixed reagent compound and stabilizing agent are substantially dissolved to form the aqueous composition thereof.

36. The composition of claim 35 further characterized in that said composition is used in conjunction with a buffer composition comprised of a mixture of a buffer compound and a magnesium compound, said mixture being present in a water containing liquid to form an aqueous buffer composition such that the buffer compound is present in the buffer composition to create a proper pH range for a phosphatase enzyme determination.

37. The composition of claim 35 further characterized in that said stabilizing agent is phenol and phenolic compounds.

38. The composition of claim 35 further characterized in that said diagnostic reagent compound is a labile substrate used in determination of a phosphatase enzyme.

39. The composition of claim 35 further characterized in that said reagent compound is a labile substrate used in phosphatase enzyme determination, said substrate is paranithrophenolphosphate and said stabilizing agent is phenol and phenolic compounds.

40. A method of preparing aqueous liquid reagent systems used in phosphatase enzyme determination, said method comprising forming a substrate composition by stabilizing a labile organic diagnostic reagent substrate against hydrolysis in a hydrolysis reaction and which reaction is represented by:

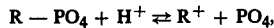
$$R - PO_4 + H^+ \rightleftarrows R^+ + PO_4,$$
where $R - PO_4$ represents a cyclic or aromatic group with a phosphate moiety thereon and $PO_4$ represents a phosphate group hydrolyzed therefrom and $R^+$ represents a reaction product based on R with the phosphate moiety hydrolized therefrom, said reaction normally proceeding to saturation in absence of any stabilization against hydrolysis, said method comprising mixing said reagent substrate with a stabilizing agent selected from the class consisting of (1) phenol and phenolic compounds, (2) imidazol and (3) nitro aliphatic groups containing from 1 to 6 carbon atoms, said stabilizing agent approximating the effect of the cyclic or aromatic group without the phosphate moiety thereon as a reaction product or portion thereof in a hydrolysis reaction, or the effect of the phosphate moiety which would be produced in a hydrolysis reaction, and which thereby inhibits a hydrolization reaction of said substrate, said substrate being specific with respect to a phosphatase enzyme such that the enzyme will be affected by the substrate or the end product in a determination reaction or both and will not be affected by the stabilizing agent, introducing the mixed reagent substrate and stabilizing agent into a water containing liquid to form an aqueous solution thereof, and storing said solution in a container.

41. The method of claim 40 further characterized in that said method comprises mixing a buffer compound with a magnesium compound to form a mixture thereof, and introducing said mixture into a water containing liquid to form an aqueous buffer composition such that the buffer compound is present in the buffer composition to create a proper pH within the desired range for a phosphatase enzyme determination, and storing said buffer composition in a separate container.

42. The method of claim 40 further characterized in that said substrate is paranitrophenolphosphate or salts thereof and said stabilizing agent is phenol or a phenolic compound.

43. The method of claim 42 further characterized in that the substrate is present in an amount from about 100 millimoles to about a saturation level, and said stabilizing agent is present in an amount from about 100 millimoles to about at least twice the amount of substrate.

44. A stabilized liquid reagent system used in phosphatase enzyme determination, said system comprising a substrate composition comprised of a labile organic diagnostic reagent substrate having a general formula $R - PO_4$ and which is stabilized in an aqueous solution against hydrolysis in a hydroysis reaction and which reaction is represented by:

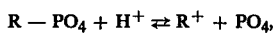
$$R - PO_4 + H^+ \rightleftarrows R^+ + PO_4,$$
and where $R - PO_4$ represents a cyclic or aromatic group with a phosphate moiety thereon and $PO_4$ represents a phosphate group hydrolyzed therefrom and $R^+$ represents a reaction product based on R with the phosphate moiety hydrolized therefrom, said reaction normally proceeding to saturation in absence of any stabilization against hydrolysis, said reagent substrate being stabilized in the presence of a stabilizing agent selected from the class consisting of (1) phenol and phenolic compounds, (2) imidazol and (3) nitro aliphatic groups containing from 1 to 6 carbon atoms, said stabilizing agent approximating the effect of the cyclic or aromatic group without the phosphate moiety thereon as a reaction product or portion thereof in a hydrolysis reaction, or the effect of the phosphate moiety which would be produced in a hydrolysis reaction, and which thereby inhibits a hydrolization reaction of said substrate, said substrate being specific with respect to and used in a determination of a phosphatase enzyme such that the enzyme will be affected by the substrate or the end product in a determination reaction or both and will not be affected by the stabilizing agent, the mixed reagent substrate and stabilizing agent being substantially disolved in a water containing liquid to form an aqueous solution thereof, and said solution being stored in a container.

45. The composition of claim 44 further characterized in that said composition is used in conjunction with a buffer composition comprised of a mixture of a buffer compound and a magnesium compound, said mixture being present in water containing liquid to form an aqueous buffer composition such that the buffer compound is present in the buffer composition to create a proper pH within the desired range for a phosphatase enzyme determination.

46. The composition of claim 45 further characterized in that said substrate is paranitrophenolphosphate or salts thereof and said stabilizing agent is phenol or a phenolic compound.

47. The composition of claim 46 further characterized in that the substrate is present in an amount from about 100 millimoles to about a saturation level, and said stabilizing agent is present in an amount from about 100 millimoles to about at least twice the amount of substrate.

* * * * *